United States Patent
Weber et al.

(10) Patent No.: US 6,699,237 B2
(45) Date of Patent: *Mar. 2, 2004

(54) TISSUE-LIFTING DEVICE

(75) Inventors: Paul J. Weber, Fort Lauderdale, FL (US); Michael Robert Weber, Palm Harbor, FL (US); Luiz B. Da Silva, Danville, CA (US)

(73) Assignee: Pearl Technology Holdings, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/037,053

(22) Filed: Dec. 31, 2001

(65) Prior Publication Data

US 2002/0128648 A1 Sep. 12, 2002

Related U.S. Application Data

(63) Continuation-in-part of application No. 09/475,635, filed on Dec. 30, 1999, now Pat. No. 6,440,121, and a continuation-in-part of application No. 09/478,172, filed on Jan. 5, 2000, now Pat. No. 6,432,101, and a continuation-in-part of application No. 09/588,436, filed on Jun. 6, 2000, now Pat. No. 6,391,023, and a continuation-in-part of application No. 09/749,497, filed on Dec. 22, 2000.

(51) Int. Cl.$^7$ .............................................. A61B 18/18
(52) U.S. Cl. ................................. 606/2; 606/9; 606/13
(58) Field of Search ............................ 606/9, 27–45, 606/48–52

(56) References Cited

U.S. PATENT DOCUMENTS

| 5,514,131 | A | * | 5/1996 | Edwards et al. | 606/45 |
| 6,033,398 | A | * | 3/2000 | Farley et al. | 606/27 |
| 6,135,999 | A | * | 10/2000 | Fanton et al. | 606/45 |
| 6,203,540 | B1 | * | 3/2001 | Weber | 606/15 |
| 6,391,023 | B1 | * | 5/2002 | Weber et al. | 606/15 |
| 6,419,674 | B1 | * | 7/2002 | Bowser et al. | 606/45 |
| 6,432,101 | B1 | * | 8/2002 | Weber et al. | 606/2 |
| 6,440,121 | B1 | * | 8/2002 | Weber et al. | 606/2 |
| 6,461,357 | B1 | * | 10/2002 | Sharkey et al. | 606/45 |

\* cited by examiner

*Primary Examiner*—Michael Peffley
*Assistant Examiner*—Peter Vrettakos
(74) *Attorney, Agent, or Firm*—John P. Wooldridge

(57) ABSTRACT

A device is described that can be used by surgeons to provide accurate tissue-lifting and tightening maneuvers that uses minimal external incisions, enhances accuracy, reduces inadvertent consequences while speeding the procedure. The device is comprised of a shaft with a relatively planar but possibly lenticulate or even slightly curved tip that can divide and energize various tissue planes causing net contraction via the fibrous tissue modification. Various forms of energy can also be delivered to cause desirable tissue alterations.

31 Claims, 2 Drawing Sheets

TISSUE-LIFTING DEVICE

This application is a continuation-in-part of U.S. patent application Ser. No. 09/475,635, now U.S. Pat. No. 6,440,121 titled "Surgical Device for Performing Face-Lifting Using Radiofrequency Energy", filed Dec. 30, 1999, incorporated herein by reference, U.S. patent application Ser. No. 09/478,172, now U.S. Pat. No. 6,432,101 titled "Surgical Device for Performing Face-Lifting Using Electromagnetic Radiation", filed Jan. 5, 2000, incorporated herein by reference, U.S. patent application Ser. No. 09/588,436, titled "Thermal Radiation Facelift Device", filed Jun. 6, 2000, now U.S. Pat. No. 6,391,023 incorporated herein by reference, and U.S. patent application Ser. No. 09/749,497, titled "Face-Lifting Device", filed Dec. 22, 2000, incorporated herein by reference.

BACKGROUND OF THE INVENTION

1. Field of the Invention

The invention relates to face-lifting devices, and more specifically, it relates to a surgical device that can quickly and safely separate tissue planes. In addition, the invention relates to a face-lifting device that can apply energy to tissue to induce tightening.

2. Description of Related Art

Definitions, Critical Anatomy and Nomenclature:

Cutting (in surgery) is herein defined as relatively cleanly breaking through similar or dissimilar tissues with minimal adjacent tissue trauma and thus little tissue stretching, tearing or ripping. Lysis (in surgery) is herein defined as breaking through similar or dissimilar tissues with or without adjacent tissue trauma and may involve stretching, tearing or ripping. Depending upon the tissues lysed, the degree of stretching or tearing of lysed tissue edges may be inconsequential or may even result in a desirable benefit such as post surgical contraction. Planes of tissue are not often flat and represent the curviform intersection of dissimilar tissues and are made at least partly of fibrous tissues, either loose and spongy or firm and tough. Planes between the soft internal organs are usually loose and spongy. Planes of tissues in the face and on bones are firm and tough. Undermining is herein defined as tissue separation either within or between defined tissue planes. Undermining may be sharp (instrument) or dull (instrument) depending upon the amount of fibrous tissue binding or existing between the tissue planes to be separated. Undermining is usually performed, as is most surgery, with the intention of minimizing trauma. Sharp instrument undermining is usually performed to separate highly fibrous or collagenous tissues; however, sharp undermining suffers from the risk of penetrating adjacent tissues inadvertently because of loss of ability to follow the desired plane. Inability to follow or maintain the plane in sharp undermining is frequently due to limited visibility, difficulty "feeling" the fibrous plane, or scarring (collagen fibrosis) resulting from previous trauma or surgery. Even experienced surgeons may from time to time lose the correct plane of sharp undermining; great skill is required. Blunt undermining allows a rounded, non-sharp tipped, instrument or even human finger to find the path of least resistance between tissues; once the desired plane is found by the surgeon, it is easy to maintain the plane of blunt undermining until the task is complete. Unfortunately, blunt undermining between highly fibrous tissues such as the human face usually causes tunneling with thick fibrous walls. Dissection usually implies sorting out and identification of tissues and usually implies that some sort of undermining has been performed to isolate the desired structure(s). In face-lifting surgery, plastic surgeons have so commonly used the terms undermining and dissection interchangeably that they have become synonymous in this specific situation. Tracking means to maintain a direction of movement upon forcing a tissue-separating instrument without unpredictable horizontal movement or leaving the desired tissue plane(s). Planar tracking means to stay in the same tissue planes. Linear tracking means to move uniformly in a straight or uniformly curved path without unpredictable movement. Groups of linear tracks may form a network that creates an undermined tissue plane.

Disadvantages of the current face-lifting and brow-lifting techniques are numerous and have resulted in undesirable outcomes and litigation. Face-lifting and tissue-tightening devices described in the prior art resemble undermining devices that were constructed with cutting edges that rely entirely on the skill of the surgeon to maintain control. Inadvertent lateral cutting or tissue trauma may be difficult to control. Thus, tissue positioning of a cutting edge is the paramount problem with current face-lifting/undermining technology. In addition, speed of separation is important to reduce the time that the patient is exposed to anesthetic drugs; time duration of anesthesia may be directly related to the risk of anesthetic complications. Use of prior art undermining devices (including scissors, sharp rhytisectors, etc.) in these planes during cosmetic surgery has, at times, resulted in unwanted cutting, trauma or perforation of adjacent structures. Scissors and rhytisectors are planar cutting instruments; thus, the position of the cutting edges with respect to the surface of the face is controllable only by the surgeon who must estimate cutting edge's location, as no intrinsic third dimensional limitation to movement exists in the instrument. Unfortunately, scissors with 3 dimensional or "bulbous", spheroidal tips cannot close completely to cut or define a plane in target tissues. Scissors with 2 dimensionally rounded tips can close all the way to cut target tissue however the shape and tips are prone to inadvertently wander undesirably between tissue planes because of a lack of a third dimensional limitation.

Current electro surgical devices for use in general surgery must be delivered through large open pockets or through the limited access, slow moving and tedious endoscopes if they are to see use in the aforementioned settings. U.S. Pat. No. 5,776,092 by Farin describes a single tube device that can deliver laser, ultrasound or radio frequency devices to treat tissue. However, Farin's device is not intended for separating tissue planes and is susceptible to catching, tearing or puncturing the tissue when manipulated. It would be advantageous to provide a device for the precise application of energy to proper face-lift tissues to be separated and energized while excluding vital structures such as nerves and delicate vessels and maintaining an exact distance from the very delicate surface of the skin. It would be additionally advantageous for the same provisions to allow for a uniform forward tracking and feel of motion of the device that provides a surgeon with instantaneous knowledge. Properly sized and placed bulbs and lysing segments address all of these problems in a manner not previously possible.

Just as sharp undermining or dissection has its disadvantages, as previously mentioned, blunt dissection suffers from its own difficulties as well. Forcing a blunt object through tissue avoids indiscriminate sharp cutting of important structures (nerves, vessels). Blunt undermining compacts the stronger, firmer, strands of collagen even contained within tissues as soft fat into thicker "bands" (some overly thick for uniform cutting). However, disadvantageously for the aforementioned intentions, traditional purely-blunt-object undermining often results in random motion or uncontrollable-slippage of the underminer tip on forward motion and thusly loss of precise tracking of the underminer through target tissue. Additionally, thickened devices often "hang-up" or get caught in various tissue structures for example collagenous bands.

Currently it takes many surgeons varying amounts of time often exceeding 10–20 minutes and even an hour to dissect the scalp brow-lifting plane and coagulate blood vessels, especially if coagulation is needed for unsealed emissary vessel trauma. It is desirable to provide a tissue-lifting device that would reduce time for a surgeon to do both tissue plane separation and coagulation as well as aids in maintaining proper tissue positioning and tracking through the appropriate layers. The operative time reduction should exceed 90%. Reduced operating time means less time a wound is open to potential sources of infection, lowered surgical costs less operating room time, less risk under anesthesia, and thus a general improvement in the procedure.

SUMMARY OF THE INVENTION

It is an object of the present invention to provide a method and a device that can be used by surgeons to quickly and safely separate tissue planes.

It is another object of the invention to provide a facial tissue lifting and facial tissue-tightening device that easily maintains the proper dissection plane by constraining the position of the lysing segments within the desired tissue layers.

Another object of the invention is to provide an undermining device that can position lysing surfaces at a proper level for controlled and safe fibrous tissue separation during a brow-lift.

In one embodiment the device is comprised of a hollow or solid shaft with a relatively planar tip that can be easily positioned between dissection planes in tissue and then manipulated to separate tissue planes and lyse fibrous tissue. Thermal effects of externally applied energy transmitted to the collagenous (dermal, superficial platysma musculature and other) tissues of the face in the facelift plane can cause cosmetically desirable contraction of the dermal tissues with beneficial tightening of the facial tissues. Accordingly, the invention provides an internally transmissible energy source and delivering means, which delivers energy to the distal end of the shaft. Various forms of energy may be used to augment tissue change in the wake of instrument passage including lasers, thermal, and RF and ultrasound energy.

One embodiment of the invention has a plurality of bulbous-tissue-positioning members on the distal end of the shaft separated by at least one interstitial lysing segment. The lysing segments are powered by an RF energy source (e.g., finesse electrosurgical generator, Utah Medical Products, Inc.). The energized lysing segment is thiner than the positioning bulbous members and usually recessed from the distal tip. However, in an alternative embodiment the energized lysing segments may be flush with the distal tips or may even extend or protrude beyond the distal tip of the bulbous positioning members. In this embodiment tissue above and below the lysing plane is protected from the energized lysing segment by the top and bottom surfaces of the bulbous members. For the purposes of this patent application, the term 'bulb' or 'bulbous' will include a variety of shapes such as spheroidal, conical, ellipsoidal, or faceted. Captured rolling balls or spheres could also be used as the bulbous members.

Although an embodiment provides a shaft that has a cross-sectional shape that is approximately rectangular, acceptable alternative versions of the shaft may be oval, semi-circular, or trapezoidal in cross-section. Although an embodiment provides a tip having a shape with alternating protrusions and recessions, acceptable alternative versions of the tip shape may be semicircular, lenticulate or geometric. The same protrusions that exclude critical anatomical structures (such as blood vessels or nerves) by virtue of their relationship to the cutting recessed segments also serve to position the depth of the present invention with respect to various tissues such as the lower dermal layer of the face. The spacing and the relationship of the protrusions (bulbs) and lysing segments aid in maintaining proper tracking of the instrument when the surgeon forces the instrument through the target tissue to be treated. The beneficial feeling of "tracking" is instantly palpable by the surgeon on forced device motion; thus the surgeon requires no monitor to know how the device is moving. Both the number and spacing of bulbous-structures will aid in reducing wobble or lateral (horizontal) slippage during forward thrusting of the shaft. Vertical slippage of the instrument within tissue is prohibited if a properly directed upward force is applied by the surgeon's hand with forward passage of the instrument. This is because the width of the protrusions/bulbs helps maintain the correct distance between the lysing segments and the delicate underside of the superficial skin or dermis.

Beneficially, the tip of the device and the action of the device can be felt/appreciated without direct visualization (endoscope). The surgeon can blindly and confidently know that the device is tracking in the proper tissue plane and location. The feel of the device in the proper tissue plane is easily learned since measurable resistance without visualization through the facial tissues can immediately tell the surgeon the location and the amount of undermining that has occurred at that location.

A method description of a typical brow-lifting surgical procedure with the brow-lifting version of the device is as follows. The patient desiring the brow lift undergoes preoperative marking and shampooing with a germicidal solution such as chlorhexidine with care to avoid the eyes and ears. Preferably (but not limited to) six preoperative ink marks are made onto right and left posterior frontal, right and left mid parietal and right and left posterior parietal scalp skin. The scalp hair is then partitioned and grouped with elastic or metal wires to provide proper exposure to the expected incision. Most desirably, an anesthesiologist or nurse anesthetist may intravenously sedate the patient prior to local anesthetic injection (lidocaine with adrenaline or even tumescent solution). Less desirably, general anesthesia may be used in place of IV sedation. Following a desired level of sedation comfort or general anesthesia, the scalp is ready for local anesthesia injection or tumescent solution injection. Ring blocks of injectable local anesthetic (lidocaine or bupivicaine) may be administered by syringe for enhanced pain control. One to two centimeter long, sagitally-directed, scalpel or laser incisions made through the scalp skin and fatty layers into the galeal layer at the previously described markings provide for entrance portals for the brow-lifting device. The device is placed in one or several of the incisions and activated electrically while being manually forced forward and pulled backward in the galeal/subgaleal plane along the contour of the skull from ear to ear, from frontal hairline to uppermost neck/lower occiput. Full scalp mobilization or detachment from the skull in a bloodless manner should result. Following use of the novel device herein described, endoscopic brow lifting (already well-described in the surgical literature) can take place using as portals the two frontal scalp incisions. Following the endoscopic portion of the brow-lift, the entire scalp is rotated posteriorly thus raising the forehead/brow; the rotated scalp is fixed into its new position against the skull using absorbable or non-absorbable screws. The screws secure one or more of the scalp layers and/or edges of preferably all of the incisions (but possibly less) to the underlying bony skull. Sutures, staples, antibiotic ointments, and dressings may then be placed as desired to conclude the procedure.

These and other objects will be apparent to those skilled in the art based on the teachings herein. Other objects and advantages of the present invention will become apparent from the following description and accompanying drawings.

DETAILED DESCRIPTION OF THE INVENTION

The present invention provides a device to be used by surgeons that provides quick and accurate face lifting and brow lifting maneuvers and maximizes efficiency, reduces bleeding and is capable of tissue modification via various energy applications. The device is comprised of an undermining shaft with or without specialized tips or energy delivering windows that can easily travel along dissection planes within tissue and be manipulated to separate tissue planes and lyse fibrous tissue as well as alter tissue planes via energy application.

Figure 1:
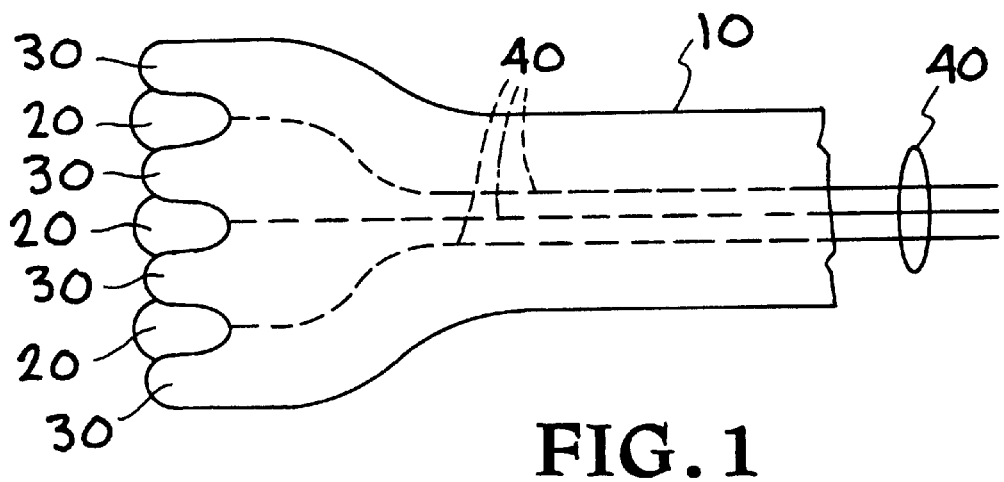
FIG. 1 shows a partial top view of the distal tip of an embodiment of the tissue-lifting device apparatus of the present invention.

FIG. 1 shows a partial top view of the distal tip of an embodiment of a brow/face-lifting device 10 of the present invention. In some embodiments, the lysing segments (with a cutting edge) are configured to transmit electrical energy and/or RF energy, e.g., to aid in cutting or cauterizing the lysed tissue. In other embodiments, the lysing segments are not configured to transmit electrical and/or RF energy. In such cases, the lysing segments need not be formed of electrically conductive material. When such energy transmission is desired, lysing segments 20 are comprised of electrically conductive materials including metals such as surgical stainless steel, tungsten, aluminum, etc. The bulbous elements 30 adjacent the lysing segments 20 are preferably comprised of nonconductive materials such as ceramic, plastic, epoxy, resins, rubbers, glass, or the like. Electrically-conductive lysing segments are electrically connected through wires 40 in shaft 10 to an electro surgical generator such as a Valleylab Surgistat® or Utah Medical Inc. Finesse®. Shaft 10 can be any shape in cross-section (e.g., circular, oval, flat, rectangular, square, geometric, etc.). In this embodiment the distal tip of the lysing segments extends beyond the bulbous segments. Alternatively the distal tip of the lysing segments could be flush or recessed relative to the distal tip of the bulbous segments.

Figure 2:
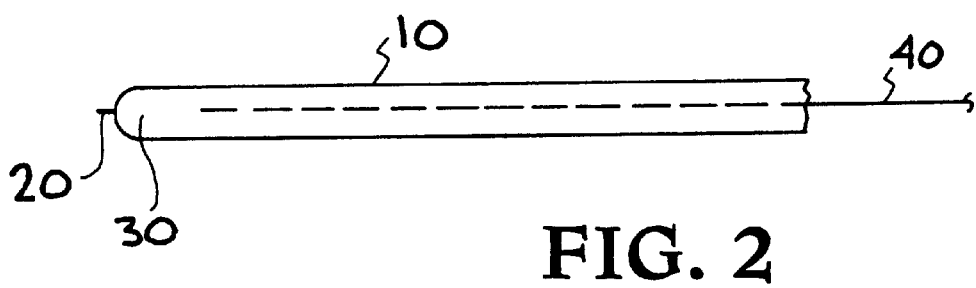
FIG. 2 is a side view of the distal tip of an embodiment of the tissue-lifting device apparatus of the present invention.

FIG. 2 is a side view of the distal tip of the brow/face-lifting device apparatus 10 of the present invention. In this embodiment the top and bottom surfaces of the bulbous segments 30 protect sensitive tissue from the lysing segment 20. As shown in this embodiment the distal tip of the lysing segments 20 extends beyond the bulbous segments. In an alternative embodiment the distal tip of the lysing segments could be flush or recessed relative to the distal tip of the bulbous segments.

Figure 3:
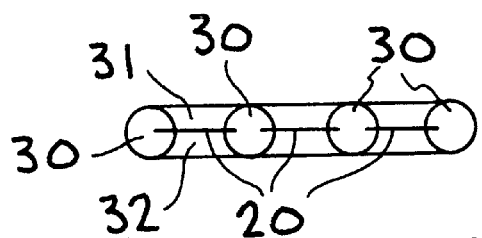
FIG. 3 is a frontal-horizontal view of an embodiment of the distal tip of the tissue-lifting device of the present invention.

FIG. 3 is a frontal-horizontal view of the distal tip of an embodiment of the tissue-lifting device 10 of the present invention. The lysing segments 20 are within indentations 31 and 32 located between the bulbous elements 30. In an alternative embodiment, the indentations are removed and the top and bottom surfaces of the bulbous elements are planar. Removing the indentations increases the risk of lysing sensitive tissue and also reduces the tracking capabilities of the device.

Figure 4:
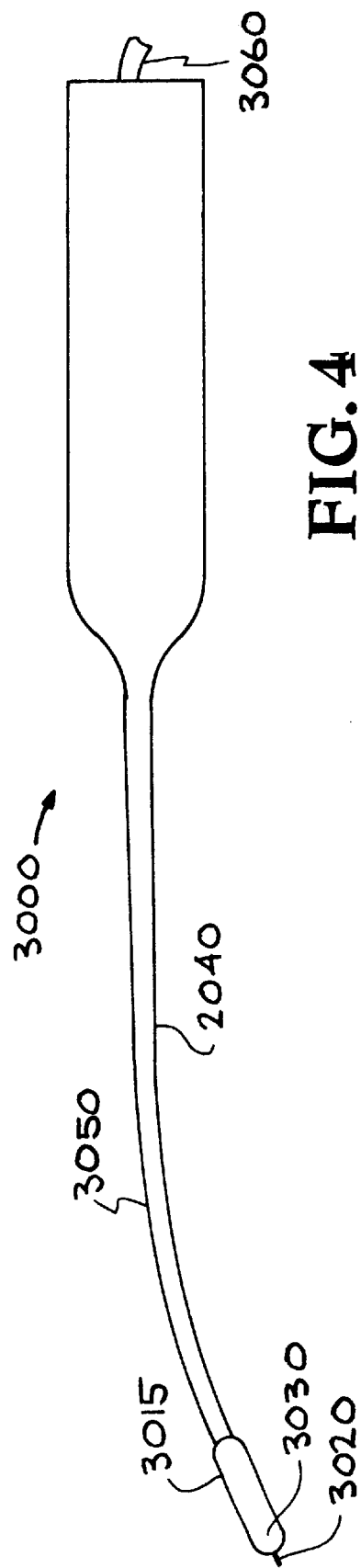
FIG. 4 is a side view of an embodiment of the brow-lifting version of the tissue-lifting device of the present invention.

FIG. 4 is a side view of the device 3000 that is optimized for brow-lifting. For brow-lifting the shaft 3050 of the device is curved to conform to the skull and limited space between the galeal scalp layer and the skull. The curviform shaft 3050 connects the distal tip 3015 containing lysing segments 3020 between bulbous segments 3030. The electrically-conductive lysing segments 3020 are electrically connected through electrical wires in the shaft 3050 and cable 3060 to an electro surgical generator such as a Valleylab Surgistat® or Utah Medical Inc. Finesse®.

Figure 6:
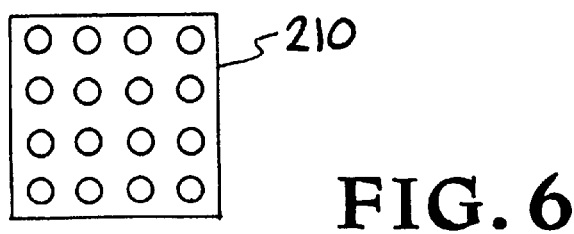
FIG. 6 shows an energy delivery element configured in an array.
Figure 5:
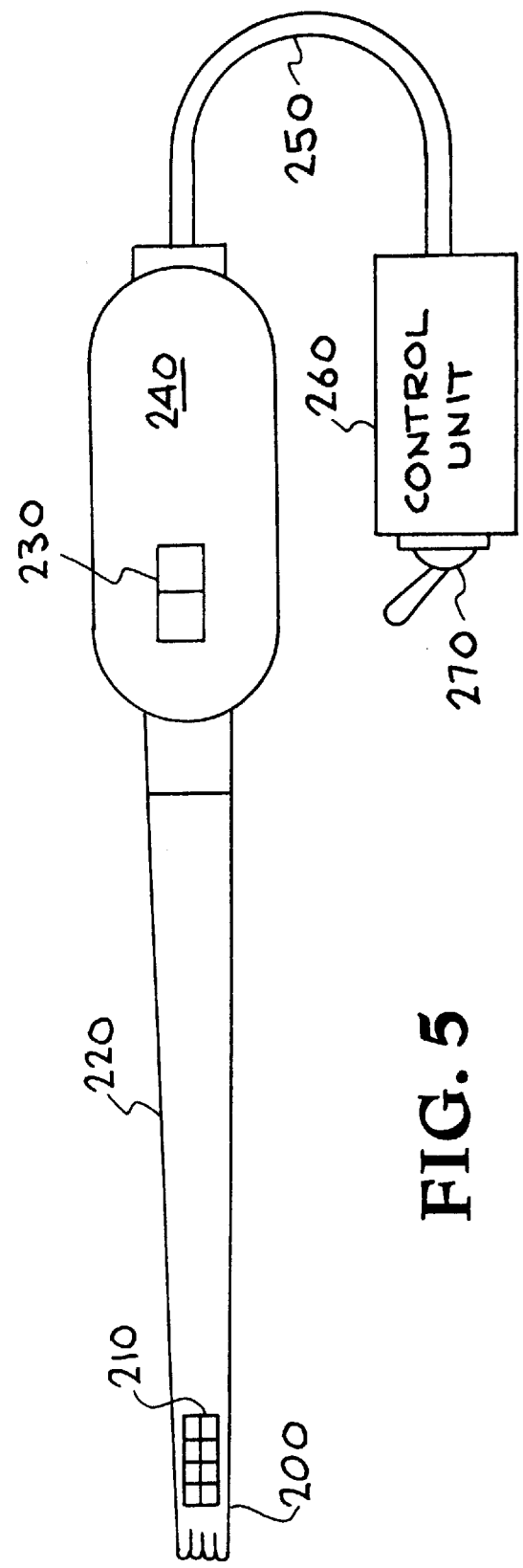
FIG. 5 is an enlarged plan or top view of the present invention that includes an additional energy delivery element to treat tissue after lysing.

FIG. 5 is a schematic illustrating the key elements of a brow/face-lifting device that has a distal tip 200 and an energy delivery element 210 located near the distal tip of the shaft 220. The energy delivery element can be an electrode that delivers RF or electrical energy, an optical window that transmits laser energy, an ultrasound transducer, a thermal source (e.g., a hot plate) and/or a microwave source. The energy delivery element 210 can be configured in an array, as shown in FIG. 6. An optional switch 230 on the handle 240 activates the lysing 200 and energy delivery elements 210. A cable 250 connects the device to a control unit 260. The control unit 260 can include power controls 270 for both the lysing 200 and energy delivery elements 210. Additional details of this integrated device can be found in the parent applications.

In some cases it may be desirable to build the device in such a way that it is usable only once or for a predetermined time or number of uses. This can be accomplished in a variety of ways such as (i) having a microchip in a sterilizable tissue lifting device that allows a certain number of treatments and may additionally show how much use time the device has left until it shuts off, (ii) fiberoptics that transmit only so much laser light before a reflective coating inside of a plastic fiberoptic burns out the device, (iii) a chip to control any of the devices, (iv) oxidation or breakdown of electrode tips to wear them out to reduce multiple uses. The disposable device can also incorporate an identification chip (e.g., VeriChip(TM) by Applied digital solutions (www.adsx.com/verichip/verichip.html, or Smart Tokens by Datakey Inc. http://www.datakey.com/, or micoID(TM) by MicroChip Inc. www.microchip.com) that can be used by the control system to identify the disposable device and prevent reuse. The identification chip can include additional data information that is used by the control unit to calibrate the system for each device. The device could be manufactured to be non-autoclavable and made to be used a single time using the above described methods or other material properties.

The above descriptions and illustrations are only by way of example and are not to be taken as limiting the invention in any manner. One skilled in the art can substitute known equivalents for the structures and means described. The full scope and definition of the invention, therefore, is set forth in the following claims.

We claim:

1. An apparatus, comprising:
   a shaft having a proximal end and a distal end;
   a plurality of protruding members on said distal end of said shaft separated by at least one interstitial lysing segment, wherein said lysing segment is flush with or protrudes relative to said protruding members, wherein said lysing segment comprises a cutting edge; and
   means connected to said shaft for providing energy to targeted tissue.

2. The apparatus of claim 1, wherein said lysing segment and said protruding members form a tip having a longitudinal axis substantially parallel with said shaft wherein said in segment has a first cross-sectional length substantially perpendicular to said longitudinal axis, wherein said lysing segment has a second cross-sectional length substantially perpendicular to said longitudinal axis, wherein said first cross-sectional length is less than said second cross-sectional length, wherein said tip is configured to separate facial tissue substantially in a plane.

3. The apparatus of claim 2, wherein said second cross-sectional length of said tip is about perpendicular to said first cross-sectional length.

4. The apparatus of claim 1, wherein said means connected to said shaft for providing energy to targeted tissue comprises a source of electrical energy electrically connected to said lysing segments.

5. The apparatus of claim 4, wherein said shaft comprises a curved shape and is either rigid or flexible, wherein said lysing segments comprise electrically conductive material, wherein said means connected to said shaft for providing energy to targeted tissue comprises a source of electrical energy electrically connected to said lysing segments.

6. The apparatus of claim 4, wherein said means for providing energy is configured to provide electrical energy that is monopolar or bipolar.

7. The apparatus of claim 1, wherein said means for providing energy comprises means for providing thermal radiation.

8. The apparatus of claim 1, wherein a lysing segment of said at least one interstitial lysing segment comprises an electrode, wherein said means for providing energy comprises means for providing radiofrequency radiation from said proximal end of said shaft to said electrode in said lysing segment so that radiofrequency energy can be transmitted through said electrode.

9. The apparatus of claim 1, further comprising a temperature sensor fixedly connected to said shaft, wherein said temperature sensor is operatively connected near said distal end of said shaft to monitor tissue temperature.

10. The apparatus of claim 9, further comprising control electronics to control said tissue temperature.

11. The apparatus of claim 10, further comprising a user interface operatively connected to said control electronics.

12. The apparatus of claim 11, wherein said user interface comprises a touch pad.

13. The apparatus of claim 9, wherein said temperature sensor is selected from a group consisting of an infrared temperature sensor, a fiber optic fluorescence temperature sensor, a thermal resistance sensor and a thermocouple sensor.

14. The apparatus of claim 1, further comprising an ultrasound transducer within said shaft, wherein said ultrasound transducer is operatively connected near said distal end for providing ultrasound energy to said tissue.

15. The apparatus of claim 1, wherein said shaft comprises material that is both electrically non-conductive and of low thermal conductivity.

16. The apparatus of claim 15, wherein said shaft comprises material selected from a group consisting of porcelain, ceramic and plastic.

17. The apparatus of claim 1, wherein said shaft is at least partially covered with Teflon® to facilitate smooth movement of said apparatus under skin.

18. The apparatus of claim 1, further comprising means for delivering ultrasonic energy to the distal end of the shaft.

19. The apparatus of claim 1, further comprising control means for controlling the delivery of said energy to the distal end of the shaft.

20. The apparatus of claim 1, wherein at least one of the protruding members has an opening at the distal end.

21. The apparatus of claim 20, further comprising at least one lumen extending through at least a portion of said shaft and terminating at the opening.

22. The apparatus of claim 1, wherein said means connected to said shaft for providing energy to targeted tissue include means for providing energy in a plane.

23. The apparatus of claim 1, wherein said means connected to said shaft for providing energy to targeted tissue is selected from the group consisting of means for providing ultrasonic energy, means for providing radiofrequency energy, means for providing electromagnetic radiation, means for providing microwave energy and means for providing thermal radiation.

24. A tissue lifting device, comprising:
    a shaft having a proximal end and a distal end, wherein said distal end comprises a tip having a plurality of protruding segments in a planar alignment, and a cuffing segment fixedly connected between adjacent protruding segments, wherein said cutting segment has a position relative to said protruding segments that is selected from the group consisting of (i) flush with and (ii) extending from; and
    means connected to said shaft for providing energy to targeted tissue.

25. The tissue lifting device of claim 24, wherein said means connected to said shaft for providing energy to targeted tissue comprises a source of electrical energy electrically connected to said cutting segment.

26. The apparatus of claim 24, wherein said means connected to said shaft for providing energy to targeted tissue is selected from the group consisting of a source of electrical energy electrically connected to said cutting segment, means for providing ultrasonic energy, means for providing radiofrequency energy, means for providing electromagnetic radiation, means for providing microwave energy and means for providing thermal radiation.

27. The apparatus of claim 24, wherein said shaft is curved.

28. The apparatus of claim 24, wherein said shaft is flexible.

29. A tissue lifting device, comprising:
    a shaft having a proximal end and a distal end;

a plurality of protruding members on said distal end of said shaft separated by at least one interstitial lysing segment, wherein the lysing segment is flush with or protrudes relative to said protruding members, wherein said lysing segment and said protruding members form a tip wherein said tip is configured to separate tissue substantially in a plane; and means connected to said shaft for providing energy to targeted tissue.

30. The apparatus of claim 29, wherein said lysing segment comprises a cutting edge.

31. A tip for a tissue lifting device, wherein said tissue lifting device has means for providing energy to targeted tissue, said tip comprising:

a plurality of protruding segments in a planar alignment; and a cuffing segment fixedly connected to said tip and located between adjacent protruding segments, wherein said cutting segment has a position relative to said protruding segments that is selected %m the group consisting of (i) flush with and (ii) extending from.

* * * * *